Figure 1:
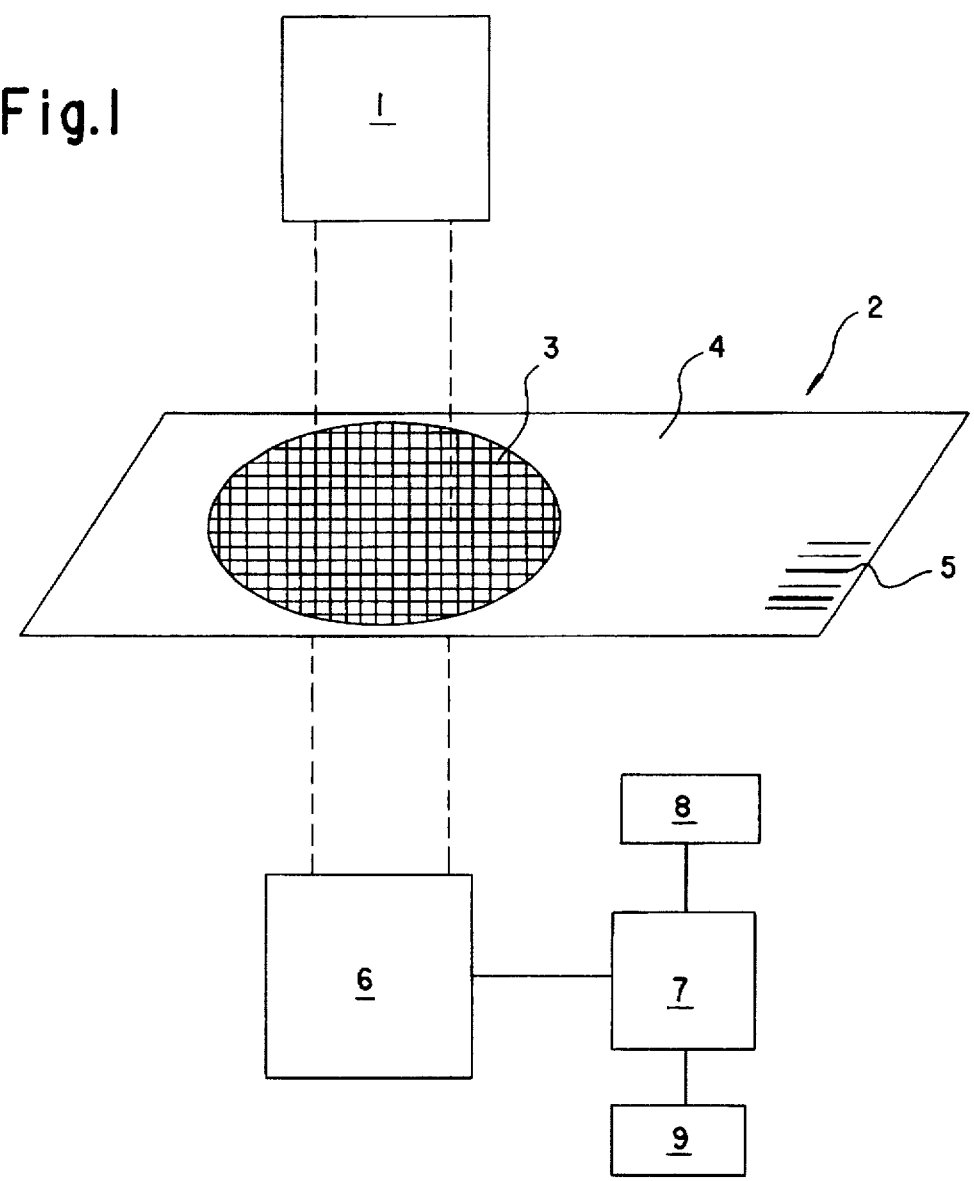

United States Patent
Böcker et al.

[11] Patent Number: 5,786,226
[45] Date of Patent: Jul. 28, 1998

[54] QUANTITATIVE TRANSMISSION SPECTROSCOPY USING SAMPLE CARRIERS WITH NETS

[75] Inventors: Dirk Böcker, Heidelberg; Gerhard Werner, Weinheim; Hans-Peter Haar, Wiesloch, all of Germany

[73] Assignee: Boehringer Mannheim GmbH., Mannheim, Germany

[21] Appl. No.: 619,935

[22] Filed: Mar. 18, 1996

[30] Foreign Application Priority Data

Mar. 16, 1995 [DE] Germany ............ 195 09 094.2

[51] Int. Cl.⁶ .......... G01N 21/35; G01N 21/25; G01J 5/02
[52] U.S. Cl. .......... 436/164; 250/339.07; 250/343; 356/244; 422/56; 422/58; 422/102; 422/104; 436/165
[58] Field of Search .......... 436/164, 165; 422/56–58, 99, 102, 104; 356/244, 246; 446/16; 250/339.07, 343

[56] References Cited

U.S. PATENT DOCUMENTS

| | | | |
|---|---|---|---|
| 3,873,268 | 3/1975 | Mckie, Jr. .................. | 422/102 |
| 4,682,890 | 7/1987 | de Macario et al. ......... | 422/102 X |
| 5,074,662 | 12/1991 | Sullivan .................... | 356/244 |
| 5,281,395 | 1/1994 | Markart et al. ............. | 422/5.8 X |
| 5,290,705 | 3/1994 | Davis ....................... | 436/164 |
| 5,445,967 | 8/1995 | Deuter ...................... | 436/164 |
| 5,453,252 | 9/1995 | Truett ....................... | 422/104 |
| 5,470,757 | 11/1995 | Gagnon et al. ............. | 436/164 |
| 5,507,288 | 4/1996 | Böcker et al. .............. | 128/633 |
| 5,519,218 | 5/1996 | Chang ....................... | 250/339.07 |

FOREIGN PATENT DOCUMENTS 644413  3/1995  European Pat. Off.

OTHER PUBLICATIONS

C. Fujimoto et al. *Anal. Chim. Acta* 1985, 178, 159–167.
J.W. Hall et al. *Clin. Chem.* 1992, 38, 1623–1631.
H. H. Eysel et al. *Appl. Spectrosc*, 1993, 47 1519–1521.

*Primary Examiner*—Arlen Soderquist
*Attorney, Agent, or Firm*—Nikaido, Marmelstein, Murray & Oram LLP

[57] ABSTRACT

Quantitative transmission spectroscopy where a sample liquid is applied onto a sample carrier having a net in such a manner that the liquid spreads across the meshes of the net. The liquid on the net is exposed to radiation essentially perpendicularly to the net, and the transmitted radiation is detected. The net accomplishes a dosing of the liquid in such a manner that identical meshes include identical quantities of liquid. For a given net, it is possible to derive the amount of liquid, which is located in a mesh and accessible to radiation, from a net constant. Knowing the amount of liquid detected by the radiation, it is possible to use the radiation absorption to calculate the concentration of one or several analytes contained in the sample liquid.

54 Claims, 1 Drawing Sheet

QUANTITATIVE TRANSMISSION SPECTROSCOPY USING SAMPLE CARRIERS WITH NETS

The invention addresses the field of quantitative transmission spectroscopy, in particular the field of infra-red spectroscopy. The invention proposes to bring a sample carrier which is provided with a net into contact with the sample liquid, so that the liquid spreads across the meshes of the net to form a liquid film. The sample carrier holding the sample liquid is exposed to a bundle of light beams which arrive essentially perpendicularly to the net. The transmitted radiation is detected, and the concentration of analyte in the sample liquid is calculated based on the detected radiation and the volume of liquid exposed to the radiation.

Prior art is in the know of quantitative infra-red spectroscopies where an exactly defined amount of sample material is applied onto a carrier which allows infra-red radiation to pass. The amount of analyte is calculated from the absorption of infra-red radiation by the sample material based on the known amount of sample material. Such a procedure is described, for example, in Clinical Chemistry vol. 38, No. 9, 1992, pages 1623–1631.

Prior art also discloses sample carriers that are provided with a net onto which the sample liquid is applied. U.S. Pat. No. 5,290,705 describes a sample carrier for optical analysis which is provided with a net having holes of varying diameters. Based on the varying sizes of the holes, the quantities of liquid, which form a freely suspended film in the respective holes, differ greatly. The use of a sample carrier with holes of different sizes in one and the same sample carrier ensures that the thickness of the liquid film present in a hole is suitable to generate a good spectrum. The use of the described sample carrier to carry out quantitative transmission spectroscopies is, however, not disclosed.

It is, hence, an object of the present invention to provide a quantitative transmission spectroscopy which does not require complex dosing steps. It is a particular object to avoid manual dosing in a range between 100 nl up to a few microliters. It was also an object of the invention to provide sample carriers which, upon establishing contact between sample carrier and sample liquid, allow dosing without involving the user. Said objects are accomplished by means of a quantitative transmission spectroscopy comprising the following steps.

Establishing contact between sample liquid and the sample carrier which has a net such that the liquid spreads across the meshes of the net and forms a film therein.

Exposing the sample carrier to a bundle of light beams essentially perpendicularly to the plane of the net in such a manner that the focussed beams completely traverse a segment of the net where the meshes are filled with a liquid film.

Detecting transmitted radiation.

Calculating the concentration of one or several analytes contained in the sample liquid based on the detected radiation and the effective volume of sample liquid detected by the light beams, while the effective volume is calculated according to the following formula $V = Q \cdot K_1$.

Q is the surface of the cross section formed by the bundle of light beams and the net, and $K_1$ is a constant of the sample carrier.

The above-mentioned object could also be accomplished with the aid of the methods which are recited in the appended claims.

A method such as the transmission spectroscopy in accordance with the invention can be used in the visible, the infra-red, or the ultra-violet light range. When using the infra-red range, only very few materials are known which exhibit sufficient transparency to light. The known materials often also have the disadvantages of being negatively affected by aqueous sample liquids. As opposed to thereto, the method in accordance with the invention has the advantage that it is independent of the optical properties of the material used which in turn renders a multitude of materials suitable for this method.

Sample carriers in accordance with the invention comprise a handle and at least one net which is attached to this handle. The handle serves the purpose of mechanically stabilizing the net and improving its handling. Said handle is preferably made of a rigid material, such as metal or plastic, including polyethylene, polystyrene, polymethylmetacrylate, etc. The handle usually has the form of a thin plate where provision is made for recesses to receive one or several nets. Nets suitable for the purpose of the invention can be made of metals, such as noble metals or even absorbent materials. Methods made of a non-absorbing material are preferred. Particularly suitable are, hence, nets made of a plastic material, such as polyethylene, polystyrene or Teflon. Suitable nets to generate infra-red spectra are manufactured by Janos Technology Inc. and available under the trade name ECRAN™ Screen Cell. The nets can be attached to the handle by means of gluing, pressing, or sealing. A description of suitable sample carriers with nets is given in U.S. Pat. No. 5,290,705. In addition to a two-piece configuration of the sample carrier consisting of handle and net, it is also possible to have single-piece sample carriers. Such carriers can be obtained by means of injection molding, for example. The manner of manufacturing suitable sample carriers by means of injection molding also indicates that the term "nets" as understood in the present invention does not only refer to structures that are commonly known under this term. The term "nets" as understood in the present invention also refers to punched, stamped, or injection-molded structures having a regular arrangement of holes.

When using a sample carrier with a net, the sample liquid is first brought into contact with the carrier net in such a manner that liquid spreads across the meshes of the net in order to form a liquid film therein. Contact can be established between liquid and net in that the liquid is pipetted onto the net. It has proven to be advantageous when the liquid, which in most cases first forms a droplet on the net, is then distributed across the net with the aid of a pipette tip or another object. A uniform distribution of the liquid across the net can also be achieved by bringing the net into contact with a wet stamp. A particularly uniform distribution of the liquid is achieved by immersing the net into the sample liquid. In this case, it is advantageous if the net is provided in a carrier which does not receive liquid outside the net. After the sample carrier has been immersed into the liquid, said carrier is wiped off to remove excess liquid. A fluid contact between excess liquid and net is thus avoided and the dosing which is accomplished by the net itself is not subject to erroneous alterations.

Experience has surprisingly shown that it is possible to use the net for dosing when certain basic conditions are observed. It has been found that liquid which is applied onto the net spreads in such a manner that the volumes of liquid are equal within each mesh, provided the meshes feature an identical geometry. In order to achieve a uniform distribution, it is critical that the liquid spread and the formation of a drop on the net be avoided. Protein-containing sample liquids, such as blood or serum can be made to spread in a suitable manner if the net has meshes between 100 μm and 2 mm. Sample liquids such as urine feature poor film-forming properties. However, it is nevertheless possible to subject such liquids to spectroscopic measurement using the sample carriers in accordance with the invention, provided that substances which enhance the film-forming properties are added to the sample liquids. Substances that increase the film-forming properties are usually those with a high protein contents, with albumins, such as bovine serum albumin, being particularly preferred.

The spreading of the sample liquid across the net can be improved by adding a detergent to the sample solution; the detergent should have the concentration of less than 1.5%. It is also possible to coat the net of the sample carrier with a detergent already during manufacturing.

The fact that identical meshes can receive identical volumes was confirmed in experiments where dyed sera of different viscosities were measured in transmission. The experiments showed that the meshes do not only enclose identical amounts of liquid, but also that the amount of liquid enclosed remain in the range of clinically relevant viscosities of sera, i.e. between 1.6 and 2.0 mPas. It is, hence, possible to determine for nets with a given geometry and material a constant indicating which amount of a liquid of a given viscosity range is retained in each mesh.

Prior art methods allow only a restricted use of quantitative transmission spectroscopic measurements in a volume range below 2.0 μl as the dosing of the volume becomes too inaccurate in this range. However, with the methods in accordance with the invention an exact dosing is not required as the amount of liquid used for the evaluation is determined in another manner. The method of the invention, hence, allows in particular those analyses where smaller sample amounts ranging between 0.2 and 2.0 μl are to be assayed.

Moreover, experience has shown that these phenomena do not only apply to the nets, but also to punched, stamped structures and even structures with directly formed holes.

Nets in accordance with the invention have a mesh diameter between 100 μm and 2 mm, preferably between 200 μm and 1.3 mm and are made of a non-absorbent material. Particularly suitable materials for nets are Fluorotex® and Scrynel®.

When a quantitative transmission spectroscopic measurement is to be carried out, the sample carriers which are provided with a liquid are exposed to a bundle of light beams arriving essentially perpendicularly to the net. For the generation of the light beams, it is possible to use prior-art spectroscopes like those manufactured by Bruker or Perkin Elmer. It is advantageous that the light beam arrive perpendicularly to the net as this ensures that a maximum amount of liquid is exposed to the light beams. It is preferred to have a bundle of light beams with a constant cross section.

In a first variant of the method, the sample liquid can be exposed to the light beams on the sample carrier in such a manner that the light beams traverse an area of the net where all meshes are filled out. The amount of sample liquid to be evaluated is in this case limited by the cross section of the concentrated light beam. In a second variant, the bundle of light beams covers meshes that are filled with liquid and also those that are empty. In this case, the amount of sample liquid to be assayed corresponds to the number of filled meshes that are covered by the light beam. Both variants detect the transmitted radiation. The amount of light absorbed by the sample liquid is determined in that the mesh is first subject to a measurement without sample liquid and then with sample liquid. Provided the absorption of the net is already known or stored in the instrument, the measuring step where no sample liquid is used can be omitted. Based on the detected absorption, it is possible to calculate the concentration of one or several analytes contained in the sample liquid. For a quantitative determination of the concentration, it is necessary to have the volume of the sample liquid which led to a decrease in the radiation. In this patent application, said volume is referred to as the effective volume. The effective volume includes only those volumes that are exposed to the light beams. The volume applied on a sample carrier does, hence, not correspond to the volume that is subject to evaluation. However, the volume available for evaluation can also be empirically determined.

For a method according to the present invention, where the amount of liquid that is exposed to radiation is limited by the surface of the cross section between light beam and net, the effective volume can be directly determined. A suitable amount of a calibration liquid, e.g. 1 μl, is applied onto the net of a given sample carrier such that the liquid spreads across the meshes of the net. The calibration liquid has an exactly defined absorption coefficient "a" or an exactly determined absorption range for the radiation used. The calibration liquid can contain one or several substances which have a known absorption range. Advantageously, the listed substances have at least one pronounced absorption maximum located in the range of the radiation used for the measurement. By using Beer-Lambert's Law, it is possible to conclude the amount of liquid which contributes to a decrease in the measuring beam from the absorption of radiation caused by the calibration liquid. In the measurement it must be taken into consideration that the intensity of the light beam is already diminished by a net without liquid. What is, hence, critical to the determination of the absorption by the calibration liquid, is the difference between the radiation of the net with calibration liquid and the same net without calibration liquid. The effective volume can then be calculated as follows:

With the absorption coefficient (a), the concentration (c), the effective volume (V) of a liquid, and the effective cross section of the light beam (Q) at the site of the sample, the formula for Beer-Lambert's Law can be given as follows:

$$\lg(I/I_0) = -a \cdot V/Q \cdot c.$$

By measuring the intensity of the transmitted radiation using an empty net ($I_0$) and a filled net (I) one obtains the effective volume (V) of the amount of liquid that is available for exposure to radiation, provided the parameters a and c of the calibration liquid as well as the surface (Q) of the cross section between light beam and net are known. With these data, it is possible to calculate the constant ($K_1$):

$$K_1 = V/Q$$

$K_1$ is a typical variable for the effective layer thickness of a liquid film that has formed.

The above calculation is based on the assumption that identical volumes of calibration liquid always generate an identical absorption regardless of their geometric arrangement in the light path. From own experiments and from prior art, it is known that Beer-Lambert's Law also applies under the conditions used for the net.

A constant $K_1$ obtained by calibration applies to a net that has a given mesh width and geometry and is made of a given material. Since the viscosity of the liquid used is critical for the volume retained in a single mesh, the accuracy of the derivation of the volume from the formula $V=Q \cdot K_1$ depends on the degree of accuracy between the viscosities of the calibration solution and the sample liquid. In experiments where sera with different viscosities were used, experience has shown that the viscosity of the liquid has a smaller influence on the liquid volume within a mesh than was originally expected. The use of the afore-mentioned formula to calculate the effective volume is, hence, suitable even when the viscosities of the calibration liquid differs relatively greatly from the one of the sample liquid.

Constant $K_1$ can be determined during manufacturing and, for example, be attached to the sample carrier in the form of a barcode. Depending on the necessary accuracy, constant $K_1$ can be indicated for each individual sample carrier, for a production lot of sample carriers or even only once for all identical sample carriers of different lots.

The determination of constant $K_2$ for a method according to the invention can be determined as was described for constant $K_1$. The only difference is that in determination of this constant, the liquid-filled meshes which are to be detected by the light beam are counted. The counting of said filled meshes can be accomplished with methods known in prior art. The net of a sample carrier can be scanned with a light beam, for example, which is smaller than the cross section of the meshes. Detecting the transmitted light beam allows differentiating between liquid-filled and non-filled meshes. Advantageously, image recognition can be accomplished with a method where a light beam of a sufficient size is directed onto the net, and the transmitted radiation is detected with a CCD array. Based on the signals generated by the CCD array, it is possible to use algorithms for pattern detections, which are commonly known in prior art, to distinguish between filled and unfilled meshes and to determine the number of filled meshes. It is, of course, also possible to determine the number of filled meshes with the bare eye or a magnifying glass.

As opposed to $K_1$, $K_2$ is a measure for the effective liquid volume retained in a mesh.

A method for the quantitative transmission spectroscopy on nets which has also proven to be quite advantageous is to select the cross section of the light beam to be smaller than the cross section of the individual meshes. It is thus possible to avoid different areas of the net, e.g. when the net is erroneously moved in the case of a maladjustment. In said preferred embodiment, only the liquid of a single mesh is exposed to radiation, and the decrease in the intensity of the measuring beam caused by the sample liquid is detected. Further, it is also advantageous to successively evaluate in this manner a multitude of meshes of the net in order to suppress statistical deviations.

In order to carry out a quantitative transmission spectroscopical measurement in accordance with the method of the invention, the constants $K_1$ and $K_2$ are first used to calculate the effective volume of the sample liquid. This effective volume and the detected/transmitted radiation are then used to calculate the concentration of one or several analytes contained in the sample liquid. In order to carry out this calculation, a microprocessor is either directly integrated in the spectrometer or the spectrometer transfers all measured data, generally the intensities according to wavelengths, to a suitable microprocessor. From prior art, e.g. in "Clinical Chemistry, vol. 38, no. 9, 1992, pages 1623–1631", it is known how to determine the concentration of analytes from the intensity of the spectrum. Since it is necessary to know the constants $K_1$ or $K_2$ for this calculation, this data must be made available to the microprocessor. A first step is to enter the constant via the keyboard to make it thus available to the microprocessor. It is, however, also advantageous if said constant is available in a coded form, e.g. as a barcode, so that it can be scanned into the microprocessor. In a particularly preferred embodiment, only one type of sample carrier or a limited number of different types of sample carriers is used in the apparatus, and the latter is equipped with a feature to identify the type of sample carrier used. A simple identification system suitable for this purpose is commonly used in the field of photography. Modern small cameras are equipped with an electronic scanning device to identify the light sensitivity of the film used in the camera. If only one type of sample carrier is used in the apparatus for transmission spectroscopy, it is possible to store already during manufacturing the data that is specific for this particular sample carrier type.

In another embodiment of the method of the invention, the sample carrier with its net is used directly for dosing liquids. The sample carrier is brought into contact with the liquid, such that the liquid spreads across the meshes of the net in order to form a liquid film in said meshes. The now wet meshes are counted using one of the above described methods. The liquid volume (V) on the sample carrier is calculated according to the formula $V=N \cdot K_3$, wherein N is the number of the meshes wet with liquid, and $K_3$ is a constant of the sample carrier. In this case, the liquid volume (V) relates to the total volume contained in a carrier; it is, hence, different from the effective volume of the aforementioned embodiments. In addition to the effective volume of the amount of liquid available to the light beams, said volume (V) includes in this case also volume parts that are found above and below the net material. The determination of constant $K_3$ is possible by applying an exactly defined amount of liquid onto the sample carrier and determining the number of meshes wet with liquid. Constant $K_3$ is then a result of the quotient from the known volume and the number of wet meshes. Moreover, it is also possible to analytically determine constant $K_3$ by applying a liquid with a known contents of analyte onto the sample carrier and count the wet meshes of the net. The amount of liquid then available on the sample carrier is quantitatively transferred into a sample vessel and a classical analysis is carried out to determine the amount of liquid applied from the amount of analyte used. $K_3$ has the meaning of a volume that is retained by one single mesh.

The basic idea of dosing liquid by means of sample carriers with nets upon which this method is based also allows to carry out a quantitative transmission spectroscopical measurement which does not require the determination of constants such as $K_1$ and $K_2$ for the sample carriers. In this method, a known volume of sample liquid is mixed with a known volume of a calibration liquid, and the resulting mixture is applied onto a sample carrier with the net. The result of this mixing is a liquid which, due to the calibration liquid, includes an internal standard. In order to analyze the sample liquid, the resulting liquid mixture is brought into contact with a sample carrier that is equipped with a net such that a sample spreads across the meshes of the net, in order to form a liquid film in said meshes. The so prepared sample carrier is exposed to light beams and the transmitted radiation is detected. The effective volume of the calibration liquid found on the net can then be determined as a consequence of the absorption of radiation by the calibration liquid. Since the mixing ratio of calibration liquid to sample is known, it is also possible to directly calculate the effective amount of sample liquid from the determined effective volume of the mixture of liquids. Using the also measured absorption caused by the sample liquid, it is also possible to determine the concentration of one or several analytes in the sample liquid.

Using said method, it is advantageous to select the calibration liquid such that it absorbs radiation in frequency ranges which do not overlap with ranges that are necessary for the determination of the analyte. Using up-to-date evaluation methods, such as a multivariate evaluation or a discriminance analysis, it is, however, possible to use calibration liquids where the absorptions partially overlap with the absorptions of the analyte. Evaluation methods of this type are known in prior art. As an example, please refer to reference "Applied Spectroscopy, vol. 47, pages 1519–1521 (1993)".

In an important embodiment of the present invention, liquids as they are found on the net of the sample carriers are dried prior to spectroscopic analysis. This brings about the advantage that absorptions which are caused by water are greatly reduced. Analytes of great interest in clinical chemistry, such as glucose, proteins, hormones, glycerides, lipids, enzymes, pharmaceutical agents, drugs of abuse, and even electrolytes have a very low steam pressure. The detection of these substances is, hence, not negatively affected by a drying procedure. The drying of the liquids on the net may occur passively as a consequence of evaporation of the solvent or by actively using drying devices. For an example of a quantitative spectroscopy using dry samples, reference is made to the complete contents of EP-A-0 644 413. Advantageously, the drying is carried out on a horizontally placed net. This is the best way to ensure that the critical condition of the invention according to which meshes of identical geometries receive identical liquid volumes is met.

A drying of sample liquids on the net is particularly advantageous when infra-red spectroscopical methods are used, as solvents, in particular water, cause strong absorption in the infra-red range and consequently cover the absorption lanes of the analytes.

When sample liquids are dried on the net, a film will form which may tear in the course of the drying process. As was already mentioned above, the geometric arrangement of the sample in the light path has only very little influence on the applicability of Beer-Lambert's Law. A tearing of the films on the net does, hence, not cause a significant interference with the quantitative transmission spectroscopy. When making high demands on accuracy, it may be advantageous to avoid a tearing of the films on the nets. Such a tearing of the films can be prevented by selecting suitable materials for the nets. Experience has shown that nets made of a flexible plastic such as polyethylene are particularly suitable. Further, it is possible to add a detergent or a film-forming agent to the sample liquid which then also prevents a tearing of the dried films. Suitable detergents or film-forming agents are Tween 20® and Propiofan®.

Another aspect of the invention is the use of sample carriers with nets for dosing in one of the aforementioned methods. Non-absorbing materials are particularly suitable for the nets. This ensures that the applied sample liquid is not transported out of the area accessed by the radiation in an uncontrolled manner as a consequence of a capillary effect of the net.

Further, it is advantageous for the nets of the sample carrier for the meshes to have a diameter ranging between 200 μm and 1.3 mm. These sizes were selected since sample liquids such as whole blood, serum, hemolysate, and plasma which are important in clinical analysis as they form films on the nets that are suitable for transmission spectroscopy when these diameters are given.

The invention is explained in greater detail with reference to the following figures:

FIG. 1: Diagrammatic representation of a device for transmission spectroscopy.

Figure 2:
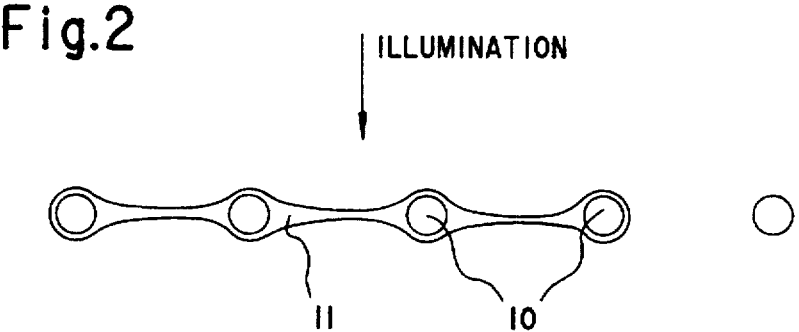

FIG. 2: Cross section of the net of a sample carrier.

FIG. 1 is a diagrammatic representation of a device for carrying out a quantitative transmission spectroscopy using sample carriers having nets. The light source (1) comprises a radiation-generating element, such as a Nernst bar or Globar and a system of lenses to focus the light beams. The bundle of light beams emitted by the light source arrives at the net (3) of the sample carrier (2). The sample carrier (2) is provided with a handle (4) to which the net (3) is attached. The carrier (4) may also contain data necessary to identify the respective sample carrier. In the example shown, a barcode (5) is provided on the sample carrier (2) which is characteristic for a constant $K_1$.

Once the light beams have passed the net (3), the focused beams arrive at a detector (6) which is part of a commonly known spectrometer for the radiation range used. The radiation is separated according to wavelength and detected, and the resulting data is made available to a microprocessor (7). Said microprocessor is connected to a barcode reader (8) to read the barcode (5) of sample carrier (2). Based on specific data of the sample carrier which is stored in the barcode and the information of the spectrum recorded, the microprocessor (7) calculates the concentration of one or several analytes. The results of this calculation are then shown on the display (9).

FIG. 2 is a cross section of a net on which a liquid film has formed. Liquid (11) forms a film between the threads (10) of the net. In cases that are relevant for the invention, where liquid spreads across the net, the liquid (11) assumes the shape of a concave lens between the individual threads (10). From FIG. 2 it can also be understood that the liquid (11) covers the threads (10) such that portions of the liquid are also located above and beneath the borders; said liquid portions are not accessible for transmission spectroscopy.

The subject matter of U.S. Pat. No. 5,290,705 is hereby incorporated by reference.

We claim:

1. A process for performing quantitative transmission spectroscopy, said process comprising the steps of:

a) contacting a sample liquid to a sample carrier, said sample carrier being provided with a net configured such that the sample liquid disperses across a plurality of openings in a mesh of the net, thereby forming a liquid film thereupon, said net having a regular mesh arrangement featuring identical mesh geometry;

b) exposing the sample carrier to a light source, wherein the light source is disposed perpendicular to a plane of the net whereby light from the light source traverses the liquid film substantially perpendicular thereto;

c) detecting light from the light source which is transmitted through the liquid film;

d) calculating a concentration of at least one analyte contained in the sample liquid based upon the detected light and an effective volume V of the sample liquid, wherein the effective volume is calculated according to the formula $$V = Q \cdot K_1$$

wherein Q is a cross section of the light from the light source where the light is exposed to the plane of the net, and wherein $K_1$ is a variable which is constant for a particular sample carrier, and is indicative of an effective layer thickness of the liquid film formed on the sample carrier.

2. A process for performing quantitative transmission spectroscopy according to claim 1, wherein said step of exposing the sample carrier to a light source comprises exposing the sample carrier to a bundle of light beams.

3. A process according to claim 2, further comprising the step of adjusting the bundle of light beams to pass through a single opening of the plurality of openings in the mesh of the net.

4. A process for performing quantitative transmission spectroscopy according to claim 1, said process comprising, before said step a), the steps of:
   1) contacting a calibration liquid to the sample carrier, said calibration liquid being selected to have a predetermined absorption coefficient, wherein the calibration liquid spreads across the openings of the mesh of the net to form a calibration film thereupon;
   2) exposing the sample carrier to the light source whereby light from the light source impinges upon of the calibration film ;
   3) detecting light from the light source which is transmitted through the calibration film;
   4) calculating the effective volume V of the calibration liquid based upon the detected light and the predetermined absorption coefficient of the calibration liquid, and calculating constant $K_1$ according to the formula $$K_1 = V/Q$$

then proceeding with step a).

5. A process according to claim 4, wherein a diameter of a light beam from the light source is less than a diameter of the calibration film.

6. A process according to claim 1, wherein the liquid film is dried before the sample carrier is exposed to the light source.

7. A process according to claim 6, wherein the sample liquid is dried when the sample carrier is in a horizontal position.

8. A process according to claim 1, wherein said contacting step is conducted by immersing the sample carrier in the sample liquid.

9. A process according to claim 1, wherein said contacting step is conducted by pipetting the sample liquid onto the sample carrier.

10. A process according to claim 1, wherein said contacting step is conducted by applying the sample liquid with a stamp.

11. A process according to claim 1, including a first step of providing a serum as the sample liquid.

12. A process according to claim 1, comprising a step of adding a detergent to the sample liquid.

13. A process according to claim 1, comprising the step of providing an infrared light source as the light source.

14. A process according to claim 1, further comprising a step of adjusting a diameter of a light beam from the light source such that the light beam passes through a single opening of the plurality of openings in the mesh of the net.

15. A process according to claim 1, wherein the sample liquid which is contacted to the sample carrier has a volume range of 1 nl to 100 µl.

16. A process according to claim 1, wherein the sample liquid which is contacted to the sample carrier has a volume range of 0.2 to 2.0 µl.

17. A process according to claim 1, wherein a diameter of a light beam from the light source is less than a diameter of the liquid film.

18. A process according to claim 1, comprising a first step of providing the sample carrier wherein the net is formed of a non-absorbing material.

19. A process according to claim 1, comprising a first step of providing each of the plurality of openings in the net with a diameter of 100 µm–2 mm.

20. A process for performing quantitative transmission spectroscopy, said process comprising the steps of:
   a) contacting a sample liquid to a sample carrier, said sample carrier being provided with a net configured such that the sample liquid disperses across a plurality of openings in a mesh of the net, thereby forming a liquid film thereupon, said net having a regular mesh arrangement featuring identical mesh geometry;
   b) counting a number of the plurality of openings having the liquid film formed thereupon;
   c) exposing the sample carrier to a light source, wherein the light source is disposed perpendicular to a plane of the net, whereby light from the light source impinges upon all of the liquid film substantially perpendicular thereto;
   d) detecting light from the light source which is transmitted through the liquid film;
   e) calculating a concentration of at least one analyte contained in the sample liquid based upon the detected light and the effective volume V of the sample liquid, wherein the effective volume is calculated according to the formula $$V = N \cdot K_2$$

wherein N is the number of openings covered with the liquid film, and wherein $K_2$ is a variable which is constant for a particular sample carrier, and is indicative of an effective liquid volume retained by one of the openings having the liquid film therein.

21. A process for performing quantitative transmission spectroscopy according to claim 20, wherein said step of exposing the sample carrier to a light source comprises exposing the sample carrier to a bundle of light beams.

22. A process for performing quantitative transmission spectroscopy according to claim 20, said process comprising, before said step a), the steps of:
   1) contacting a calibration liquid to the sample carrier, said calibration liquid being selected to have a predetermined absorption coefficient, wherein the calibration liquid disperses across a plurality of openings in a mesh of the net, thereby forming a calibration film thereupon;
   2) counting a number of the plurality of openings having the calibration film formed thereupon;
   3) exposing the sample carrier to the light source, wherein the light source is disposed perpendicular to a plane of the net, whereby light from the light source impinges upon all of the calibration film, wherein a diameter of the light is at least as great as a diameter of the calibration film on the net;
   4) detecting light from the light source which is transmitted through the calibration film;
   5) calculating the effective volume V of the calibration liquid based upon the detected light and the predetermined absorption coefficient of the calibration liquid, and calculating constant $K_2$ according to the formula $$K_2 = V/N,$$

wherein N is the number of openings having the calibration film formed thereupon;

then proceeding with step a).

23. A process according to claim 20, wherein the liquid film is dried before the sample carrier is exposed to the light source.

24. A process according to claim 23, wherein the sample liquid is dried when the sample carrier is in a horizontal position.

25. A process according to claim 20, wherein said contacting step is conducted by immersing the sample carrier in the sample liquid.

26. A process according to claim 20, wherein said contacting step is conducted by pipetting the sample liquid onto the sample carrier.

27. A process according to claim 20, wherein said contacting step is conducted by applying the sample liquid with a stamp.

28. A process according to claim 20, including a first step of providing a serum as the sample liquid.

29. A process according to claim 20, comprising a step of adding a detergent to the sample liquid.

30. A process according to claim 20, comprising the step of providing an infrared light source as the light source.

31. A process according to claim 20, further comprising a step of adjusting a diameter of a light beam from the light source such that the light beam passes through a single opening of the plurality of openings in the mesh of the net.

32. A process according to claim 20, wherein the sample liquid which is contacted to the sample carrier has a volume range of 1 nl to 100 µl.

33. A process according to claim 20, wherein the sample liquid which is contacted to the sample carrier has a volume range of 0.2 to 2.0 µl.

34. A process according to claim 20, wherein a diameter of a light beam from the light source is less than a diameter of the liquid film.

35. A process according to claim 20, comprising a first step of providing the sample carrier wherein the net is formed of a non-absorbing material.

36. A process according to claim 20, comprising a first step of providing each of the plurality of openings in the net with a diameter of 100 µm–2 mm.

37. A method for dosing liquids, comprising the steps of:
   a) contacting a sample liquid to a sample carrier, said sample carrier being provided with a net configured such that the sample liquid disperses across a plurality of openings in the mesh of the net to form a liquid film thereupon, said net having a regular mesh arrangement featuring identical mesh geometry;
   b) counting a number of the plurality of openings having the liquid film formed thereupon;
   c) calculating the liquid volume V disposed on the sample carrier using the formula $$V = N \cdot K_3$$

wherein N is the number of openings having the liquid film formed thereupon, and wherein $K_3$ is a variable which is constant for a particular sample carrier, and is indicative of a volume of sample liquid retained by one opening of said plurality of openings.

38. A method for performing quantitative transmission spectroscopy according to claim 37, wherein said step of exposing the sample carrier to a light source comprises exposing the sample carrier to a bundle of light beams.

39. A method according to claim 37, wherein said contacting step is conducted by immersing the sample carrier in the sample liquid.

40. A method according to claim 37, wherein said contacting step is conducted by pipetting the sample liquid onto the sample carrier.

41. A method according to claim 37, wherein said contacting step is conducted by applying the sample liquid with a stamp.

42. A method according to claim 37, including a first step of providing a serum as the sample liquid.

43. A method according to claim 37, comprising a step of adding a detergent to the sample liquid.

44. A method according to claim 37, comprising the step of providing an infrared light source as the light source.

45. A method according to claim 37, wherein the sample liquid which is contacted to the sample carrier has a volume range of 1 nl to 100 µl.

46. A method according to claim 37, wherein the sample liquid which is contacted to the sample carrier has a volume range of 0.2 to 2.0 µl.

47. A method according to claim 37, comprising a first step of providing the sample carrier wherein the net is formed of a non-absorbing material.

48. A method according to claim 37, comprising a first step of providing each of the plurality of openings in the net with a diameter of 100 µm–2 mm.

49. A method of quantitative transmission spectroscopy, said method comprising the steps of:
   a) mixing a predetermined volume of a sample liquid with a predetermined volume of a calibration liquid having a predetermined absorption coefficient, thereby forming a mixed sample having an internal standard;
   b) contacting the mixed sample to a sample carrier, said sample carrier being provided with a net configured such that the mixed sample disperses across a plurality of openings in a mesh of the net, thereby forming a liquid film thereupon, said net having a regular mesh arrangement featuring identical mesh geometry;
   c) exposing the sample carrier to a light source, wherein the light source is disposed perpendicular to a plane of the net;
   d) detecting light from the light source which is transmitted through the liquid film;
   e) determining absorption of light by analyses in the sample liquid and by the calibration liquid based upon the detected transmitted light;
   f) determining a volume of the mixed sample based upon the internal standard as determined by the absorption of the calibration liquid, then calculating a volume of the sample liquid based upon a mixing ratio of the predetermined volume of the sample liquid and the predetermined volume of the calibration liquid; and
   g) calculating a concentration of the analytes in the sample liquid based upon the calculated volume and the detected light.

50. A method according to claim 49, wherein the liquid film is dried before the sample carrier is exposed to the light source.

51. A method according to claim 50, wherein the sample liquid is dried when the sample carrier is in a horizontal position.

52. A method according to claim 49, wherein the sample liquid which is contacted to the sample carrier has a volume range of 1 nl to 100 µl.

53. A method according to claim 49, wherein the sample liquid which is contacted to the sample carrier has a volume range of 0.2 to 2.0 µl.

54. A method according to claim 49, wherein said step of exposing the sample carrier to a light source comprises exposing the sample carrier to a bundle of light beams.

* * * * *